(12) United States Patent
Dehghan Niri et al.

(10) Patent No.: US 9,976,989 B2
(45) Date of Patent: May 22, 2018

(54) MONITORING SYSTEMS AND METHODS FOR ELECTRICAL MACHINES

(71) Applicant: GENERAL ELECTRIC COMPANY, Schenectady, NY (US)

(72) Inventors: Ehsan Dehghan Niri, Glenville, NY (US); Curtis Wayne Rose, Mechanicville, NY (US); Andrew Batton Witney, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 232 days.

(21) Appl. No.: 14/969,893

(22) Filed: Dec. 15, 2015

(65) Prior Publication Data

US 2017/0168024 A1    Jun. 15, 2017

(51) Int. Cl.

| | | |
|---|---|---|
| *G01N 29/14* | (2006.01) | |
| *G01N 29/44* | (2006.01) | |
| *G01R 31/34* | (2006.01) | |
| *G06N 5/04* | (2006.01) | |
| *G06N 99/00* | (2010.01) | |
| *G01N 27/92* | (2006.01) | |

(Continued)

(52) U.S. Cl.
CPC ............. *G01N 29/14* (2013.01); *G01N 27/92* (2013.01); *G01N 29/2418* (2013.01); *G01N 29/4445* (2013.01); *G01N 29/4481* (2013.01); *G01R 31/1227* (2013.01); *G01R 31/343* (2013.01); *G06N 5/047* (2013.01); *G06N 99/005* (2013.01); *G01N 2291/0258* (2013.01); *G01N 2291/0289* (2013.01); *G01N 2291/2638* (2013.01)

(58) Field of Classification Search
CPC ..... G01N 29/14; G01N 29/4445; G06N 5/047

USPC ......................................................... 702/179
See application file for complete search history.

(56) References Cited

U.S. PATENT DOCUMENTS

| | | | | |
|---|---|---|---|---|
| 2010/0268042 A1* | 10/2010 | Wang | .................... | A61B 5/0059 600/322 |
| 2013/0039147 A1* | 2/2013 | Witte | .................... | A61B 5/0093 367/7 |
| 2013/0296683 A1* | 11/2013 | Herzog | ................ | A61B 5/0095 600/407 |

OTHER PUBLICATIONS

Nguyen, An-Dien. Fiber Optic Acoustic Emission Monitoring System for Condition Based Maintenance, Los Gatos Research, pp. 1-4, 2011.

(Continued)

*Primary Examiner* — Bo Fan
(74) *Attorney, Agent, or Firm* — McNees Wallace & Nurick LLC (57) ABSTRACT

A monitoring system includes an acoustic emission monitoring system including acoustic emission sensors, a partial discharge monitoring system including partial discharge sensors and synchronized with the acoustic emission monitoring system, and a computer receiving acoustic emission data from the acoustic emission sensors and electrical data from the partial discharge sensors. The computer is configured to classify a first statistical event as a fatigue cracking event by pattern recognition of the acoustic emission data and determine a first location and a first damage condition resulting from the fatigue cracking event, classify a second statistical event as a partial discharge event by pattern recognition of the acoustic emission data or the electrical data, and fuse the acoustic emission data and the electrical data for the second statistical event and determine a second location and a second damage condition resulting from the partial discharge event. Methods of monitoring are also disclosed.

18 Claims, 5 Drawing Sheets

(51) Int. Cl.
*G01N 29/24* (2006.01)
*G01R 31/12* (2006.01)

(56) References Cited

OTHER PUBLICATIONS

Janus, Patrick. Acoustic Emission Properties of Partial Discharges in the time-domain and their applications, KTH Electrical Engineering, Stockholm 2012, Electromagnetic Engineering School of Electrical Engineering, Kungliga Tekniska Hogskolan, XR-EE-ETK 2012:004.

Kane, Claude and Golubev, Alexander. Advantages of Continuous Monitoring of Partial Discharges in Rotating Equipment and Switchgear, Presented at the 2003 IEEE IAS Pulp and Paper Industry Conference in Charleston, SC.

Witos, F., Gacek Z., and Opilski, Z., Testing of Partial Discharges in Generator Coil Bars with the Help of Calibrated Acoustic Emission Method, Acta Physica Polonica A, vol. 114 (2008), No. 6-A, pp. 249-258.

Sikorski, Wojciech and Ziomek, Waldemar, Detection, Recognition and Location of Partial Discharge Sources Using Acoustic Emission Method, Published online Mar. 2, 2012, www.intechopen.com, pp. 49-74.

Su, Ching-Chau; Tai, Cheng-Chi; Chen, Chien-Yi; and Hsieh, Ju-Chu, Partial Discharge Precise Source Location Using Acoustic Emission Method for a Waveguide Functional High-Voltage Cast-Resin Dry-Type Transformer, International Journal of Applied Science and Engineering, 2009, 6, 3: 229-237.

Veloso, Giscard Franceire Cintra; Da Silva, Luiz Eduardo Borges; and Lambert-Torres, Germano, A Strategy to Locate Partial Discharges in Power Transformers using Acoustic Emission, Artificial Intelligence Applications Group, GAIA, available at http://icrepq.com/icrepq07/344-cintra.pdf, 2010.

Cho, K.B., et al., "Recent Progress and Future Perspectives on Condition Monitoring and Diagnostics for Power Equipment in Korea," International Conference on Condition Monitoring and Diagnosis, pp. 1-13 (Apr. 21-24, 2008).

Markalous, S.M., et al., "Detection and Location of Partial Discharges in Power Transformers using Acoustic and Electromagnetic Signals," IEEE transactions on dielectrics and electrical insulation, vol. 15, No. 6, pp. 1576-1583 (Dec. 2008).

Wu, M., et al., "An overview of State-of-the-Art Partial Discharge Analysis Techniques for Condition Monitoring," IEEE Electrical Insulation Magazine, vol. 31, No. 6, pp. 22-35 (2015).

Extended European Search Report and Opinion issued in connection with corresponding EP Application No. 16203940.8 dated May 11, 2017.

\* cited by examiner

MONITORING SYSTEMS AND METHODS FOR ELECTRICAL MACHINES

FIELD OF THE INVENTION

The present invention is directed to systems and methods of detection, characterization, and diagnosis. More specifically, the present invention is directed to systems and methods for the detection and characterization of fatigue cracking and partial discharge events in electrical machines.

BACKGROUND OF THE INVENTION

Fatigue cracking and partial discharge (PD) events are both issues for electric generator systems. The phenomena are related in that each may be a contributing factor of the other. Partial discharges tend to increase the number of fatigue cracks, and an increase in the number of fatigue cracks tends to increase the frequency of partial discharges. A partial discharge is a localized dielectric breakdown of an electrical insulation system that does not bridge the space between two conductors. A partial discharge generates high frequency transient current pulses that persist for a time period in the range of nanoseconds up to a microsecond. Partial discharges often begin within voids, cracks, such as fatigue cracks, or inclusions, or at conductor-dielectric interfaces within a solid dielectric. A partial discharge may also occur along the boundary between different insulating materials. Although fatigue cracking may result from any type of cyclic stresses on a material, including both mechanical and electrical stresses, the stresses are primarily electrical in the context of electric generator systems. Cumulative partial discharges may cause fatigue cracking events.

Partial discharges cause progressive deterioration of insulating materials, ultimately leading to an electrical breakdown. Repetitive PD events cause irreversible mechanical and chemical deterioration of the insulating material. Damage is caused by the energy dissipated by high energy electrons or ions, ultraviolet light from the discharges, ozone attacking the void walls, and cracking as the chemical breakdown processes liberate gases at high pressure. There are three main types of partial discharges: internal partial discharges, surface partial discharges, and corona partial discharges. A history of internal PD in a high-voltage system eventually triggers electrical treeing. A history of surface PD eventually induces insulation tracking. A history of corona PD originating in the high-voltage connections, however, is generally not harmful.

PD monitoring and detection involves evaluating the dielectric condition of a system by monitoring electrical signals and an analysis of arcing, electric field, materials, wave propagation and attenuation, sensor spatial sensitivity, frequency response and calibration, noise, and data interpretation. An electric arc is a visible plasma discharge between two electrodes that is caused by electrical current ionizing gases in the air.

The magnitude of a partial discharge is related to the extent of damaging discharges occurring and therefore is related to the amount of damage being inflicted on the insulation. The pulse repetition rate indicates the quantity of discharges occurring at the various maximum magnitude levels.

A partial discharge measurement system may include an ultra-high frequency (UHF) sensor, a high frequency current transformer (HFCT), an ultrasonic microphone, a transient earth voltage (TEV) sensor or coupling capacitor, a phase-resolved analysis system to evaluate a wide range of signal frequencies, or combinations thereof. A UHF sensor generally detects in the range of 300 MHz-1.5 GHz. An HFCT generally detects in the range of 500 kHz-50 MHz. An ultrasonic microphone generally detects in a range around 40 kHz. A TEV sensor or coupling capacitor generally detects in the range of 3 MHz-100 MHz. A phase-resolved analysis system compares pulse timing to alternating current (AC) frequency.

A significant problem with electrical detection of partial discharges is that the detection equipment is highly susceptible to electromagnetic noise, which can lead to false detection of partial discharges, typically as false positives. In high voltage systems, however, the spike caused by a partial discharge may be very small compared to the amplitude of the system voltage and may be missed, leading to a false negative. Usually the equipment subjected to testing also needs to be taken off-line, energized from a high-voltage source, and then tested, which requires a lot of time and equipment. Conventional PD measurement systems cannot detect fatigue cracks and may detect but do not locate the PD events.

An acoustic emission (AE) is a transient elastic wave within a material, typically the result of a rapid release of localized stress energy, such as when a material undergoes an irreversible change in its structure. Fatigue cracking events generate acoustic emissions.

Acoustic detection systems detect acoustic emissions as sound waves generally in the frequency range of 20 kHz up to more than 1 MHz. Acoustic detection systems may be external or internal systems. External acoustic detection systems employ sensors mounted to the outside of the equipment to be monitored. Internal systems, on the other hand, use sensors placed inside of the equipment to be monitored to directly measure the pressure wave.

An important advantage of acoustic detection over other methods is that positioning information is available by using sensors at multiple locations. This position information may help to identify the location of the source of the AE. Another advantage of acoustic detection is its immunity to electromagnetic interference or electromagnetic noise.

BRIEF DESCRIPTION OF THE INVENTION

In an embodiment, a method of monitoring a system includes synchronizing an acoustic emission monitoring system including a plurality of acoustic emission sensors and a partial discharge monitoring system including a plurality of partial discharge sensors, directing collection by the acoustic emission sensors of acoustic emission signals from the component as acoustic emission data and directing collection by the partial discharge sensors of electrical signals as electrical data, and classifying a statistical event as a fatigue cracking event or a partial discharge event by pattern recognition of the acoustic emission data and the electrical data.

In another embodiment, a method of monitoring an electric generator system includes directing collection by a plurality of first sensors on a component of the electric generator system of acoustic emission signals from the component as acoustic emission data, and classifying a first statistical event as a fatigue cracking event by pattern recognition of the acoustic emission data.

In another embodiment, a monitoring system includes an acoustic emission monitoring system including a plurality of acoustic emission sensors, a partial discharge monitoring system including a plurality of partial discharge sensors and synchronized with the acoustic emission monitoring system, and a computer receiving acoustic emission data from the acoustic emission sensors and electrical data from the partial discharge sensors. The computer is configured to classify a first statistical event as a fatigue cracking event by pattern recognition of the acoustic emission data and determine a first location and a first damage condition resulting from the fatigue cracking event, classify a second statistical event as a partial discharge event by pattern recognition of the acoustic emission data or the electrical data, and fuse the acoustic emission data and the electrical data for the second statistical event and determine a second location and a second damage condition resulting from the partial discharge event.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are systems and methods for monitoring electric generator systems and detecting and identifying partial discharge events and fatigue cracking events.

Embodiments of the present disclosure, for example, in comparison to concepts failing to include one or more of the features disclosed herein, provide detection of both partial discharge events and fatigue cracking events, determination of the location of a discharge or fatigue cracking event, a reduced sensitivity to electromagnetic noise, prediction of failure of an electric generator system at an early stage where remediation is still possible, data fusion from a PD event, enhanced measurement and characterization of a PD event, identification of a PD event as an internal, a surface, or a corona PD event, or combinations thereof.

Figure 1:
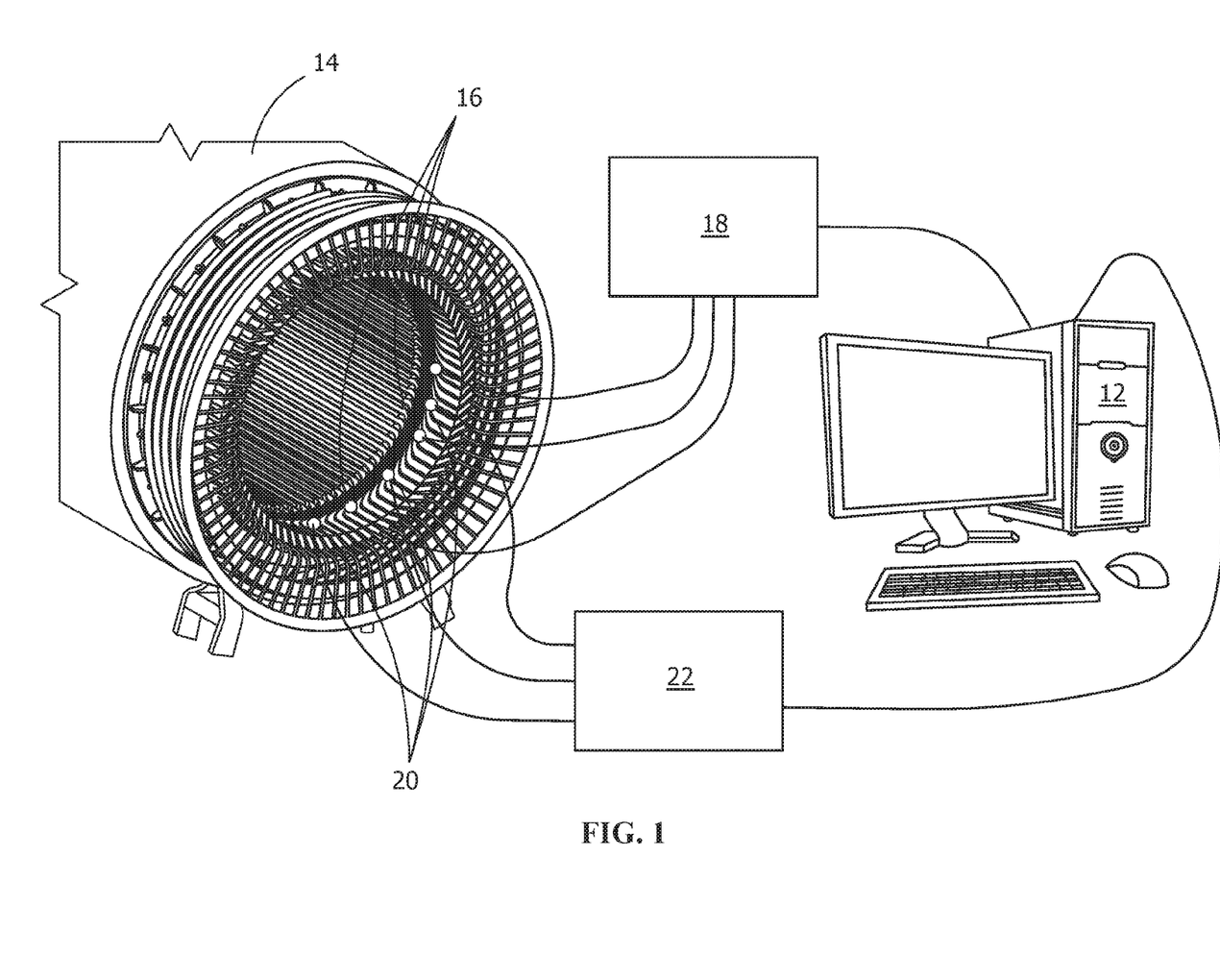
FIG. 1 is a schematic view of a monitoring system in an embodiment of the present disclosure.

Referring to FIG. 1, a monitoring system 10 includes an acoustic emission monitoring system, a partial discharge monitoring system, and a computer 12. The monitoring system 10 monitors an electric generator system 14. The AE monitoring system includes acoustic emission sensors 16 sensing acoustic emission signals from the electric generator system 14 and an acoustic emission monitoring unit 18 receiving the AE signals from the AE sensors 16 and transmitting acoustic emission data to the computer 12. The PD monitoring system includes partial discharge sensors 20 sensing electrical signals from the electric generator system 14 and a partial discharge monitoring unit 22 receiving the electrical signals from the PD sensors 20 and transmitting electrical data to the computer 12. Any type of PD sensor 20 may be used to detect electrical signals within the spirit of the present invention.

Although piezoelectric AE sensors may be used, the AE sensors 16 are preferably fiber optic AE sensors. Fiber optic AE sensors without electrically-conductive material are unaffected by the high electrical voltages of the monitored system. Fiber optic AE sensors may be embedded into the insulation material itself without causing any electrical arcing. Furthermore, the fiber optic AC sensors may simultaneously also measure strain and temperature in the system in addition to sensing acoustic emissions.

In some embodiments, the sensors 16, 20 are integrated PD/AE sensors, where each sensor 16, 20 is capable of detecting both electrical signals and AE signals. In some embodiments, the integrated PD/AE sensors 16, 20 each include a transducer integrating AE sensing and electrical-based PD sensing in one package.

In some embodiments, the monitored electric generator system is a two-pole, three-phase generator system, and the sensors are located on the six outputs (the two poles of each of the three phases) of the monitored electric generator system. In other embodiments, the electric generator system is a four-pole, three-phase electric generator system, and the sensors are located on the twelve outputs (the four poles of each of the three phases) of the monitored electric generator system.

The computer 12 receives the acoustic emission data from the acoustic emission monitoring system and the electrical data from the partial discharge monitoring system. The computer 12 is configured, either by software, hardware, user input, or a combination thereof, to classify a first statistical event as a fatigue crack by pattern recognition of the acoustic emission data and determine a first location and a first damage condition of the fatigue crack, classify a second statistical event as a partial discharge by pattern recognition of the acoustic emission data or the electrical data, and fuse the acoustic emission data and the electrical data for the second statistical event and determine a second location and a second damage condition of the partial discharge.

Figure 2:
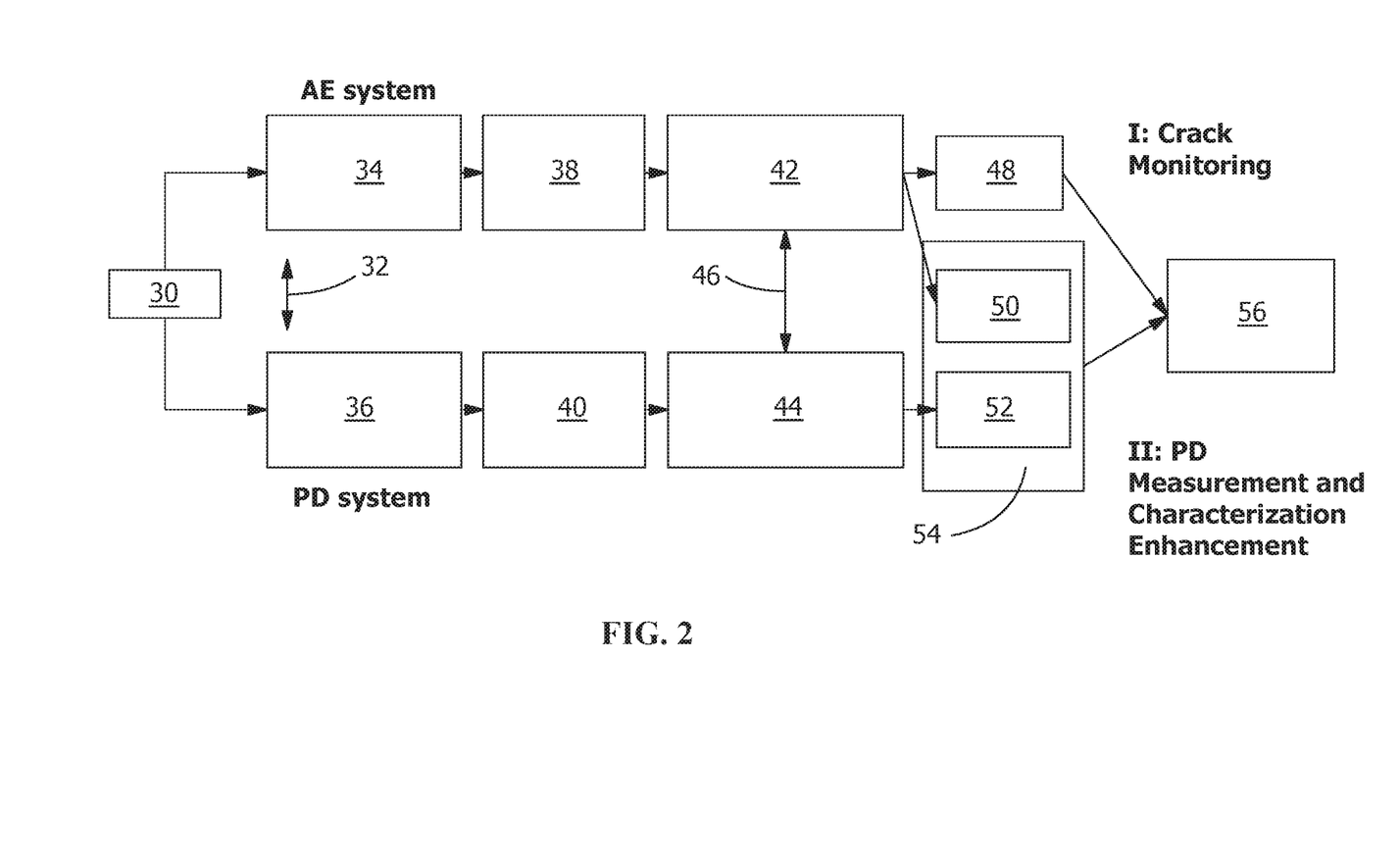
FIG. 2 is a flow chart of a method of monitoring in an embodiment of the present disclosure.

Referring to FIG. 1 and FIG. 2, a method of monitoring an electric generator system 14 includes locating acoustic emission sensors 16 of an acoustic emission detection system on a component of the electric generator system 14 and locating partial discharge sensors 20 of a partial discharge detection system on the component. In some embodiments, the component is a copper/insulator component. In some embodiments, the sensors 16, 20 are located on the lower lead connection rings, as shown in FIG. 1. The method also includes synchronizing the acoustic emission detection system and the partial discharge detection system (step 32). In some embodiments, a clock 30 synchronizes the two systems (step 32). As the detected events occur on the time scale of microseconds, as precise a synchronization as possible is desirable. The method also includes directing collection by the acoustic emission sensors 16 of acoustic emission signals from the component as acoustic emission data and directing collection by the partial discharge sensors 20 of electrical signals from the component as electrical data.

The acoustic emission detection system records acoustic emission signals as acoustic emission data (step 34) simultaneously with the partial discharge detection system recording electrical signals as electrical data (step 36). In parallel, acoustic features are extracted from the acoustic emission data (step 38), and electrical features are extracted from the electrical data (step 40). In parallel, acoustic pattern recognition classifies the acoustic features as acoustic statistical events (step 42), and electrical pattern recognition classifies the electrical features as electrical statistical events (step 44). Any appropriate pattern recognition process may be implemented within the spirit of the present invention. The acoustic statistical events and the electrical statistical events are compared as a cross-check for consistency, clarification, and confirmation of the classifications by the separate systems (step 46). Any acoustic emission data corresponding to an acoustic statistical event classified as a fatigue cracking event may be analyzed to determine the location and severity of the fatigue cracking event (step 48). Any acoustic emission data corresponding to an acoustic emission event classified as a PD event is analyzed (step 50), any electrical data corresponding to an electrical statistical event classified as a PD event is analyzed (step 52), and the acoustic emission data and the electrical data may be fused to further characterize the PD events (step 54). In some embodiments, the PD events are characterized as internal, surface, or corona PD events. The fatigue cracking event results and the PD event results are then interpreted to estimate a damage condition of the electric generator system (step 56).

Acoustic emission, as used herein, refers to the phenomenon of generation and propagation of acoustic (elastic) waves in solids that occurs when a material undergoes irreversible changes in its internal structure. For example, crack formation or an external loading, such as a partial discharge, may cause an acoustic emission.

Figure 3:
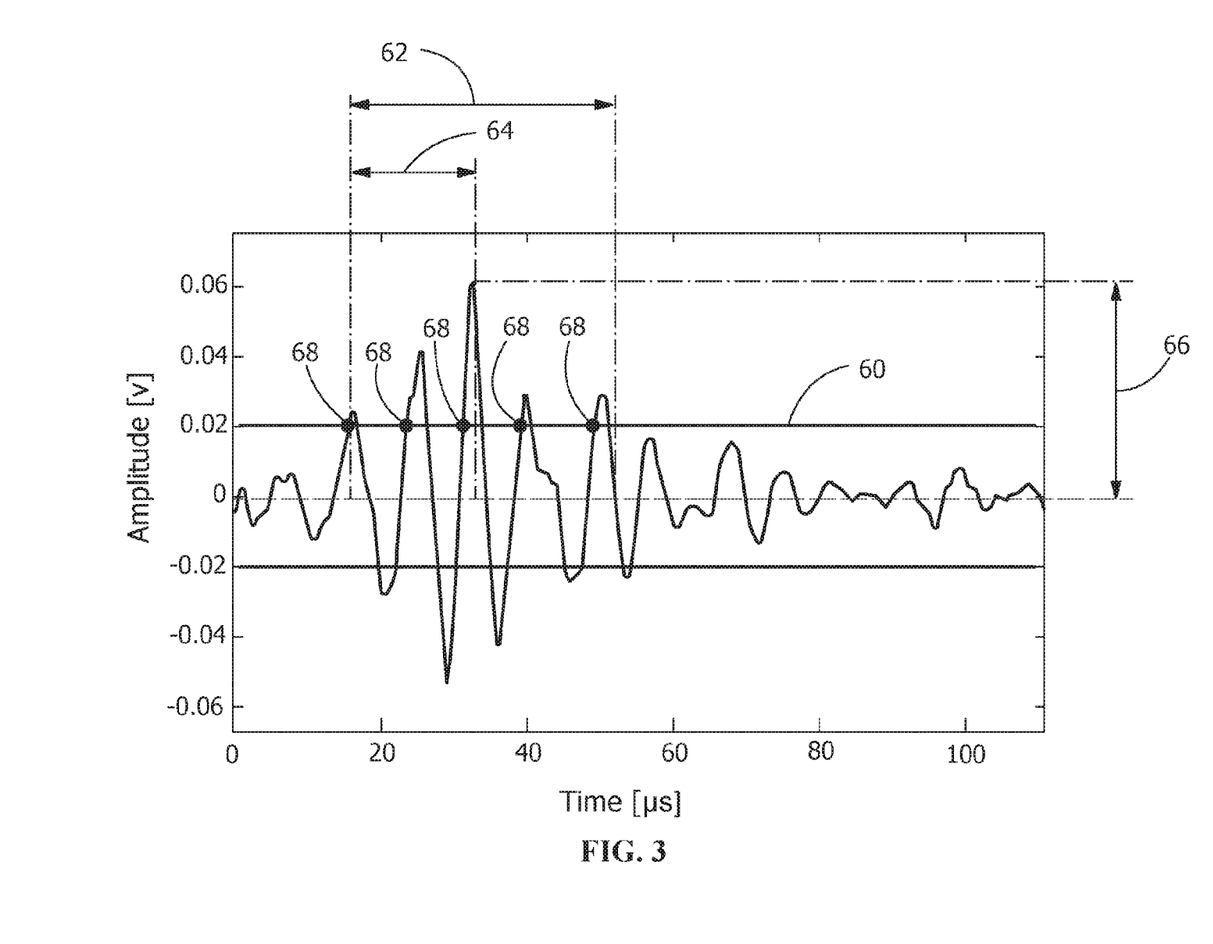
FIG. 3 is a plot of an acoustic emission signal in an embodiment of the present disclosure.

Some of the features that may be extracted from AE data are shown in FIG. 3. Feature extraction is preferably based first on defining an amplitude threshold 60 such that the system looks for peaks greater than that amplitude threshold 60. When looking for an event, the system may look for a cluster of such peaks. The duration 62 of the peaks is the time from when the first peak crosses the threshold 60 until the last peak falls below the threshold 60. The duration for the event in FIG. 3 is about 34 µs. The rise time 64 is the time from when the first peak crosses the threshold 60 until the largest peak reaches its maximum value. The rise time for the event in FIG. 3 is about 16 µs. The peak amplitude 66 is the height of the largest peak, and the counts 68 are for each time a peak goes above the threshold 60. Five such counts 68 are shown in FIG. 3.

Figure 7:
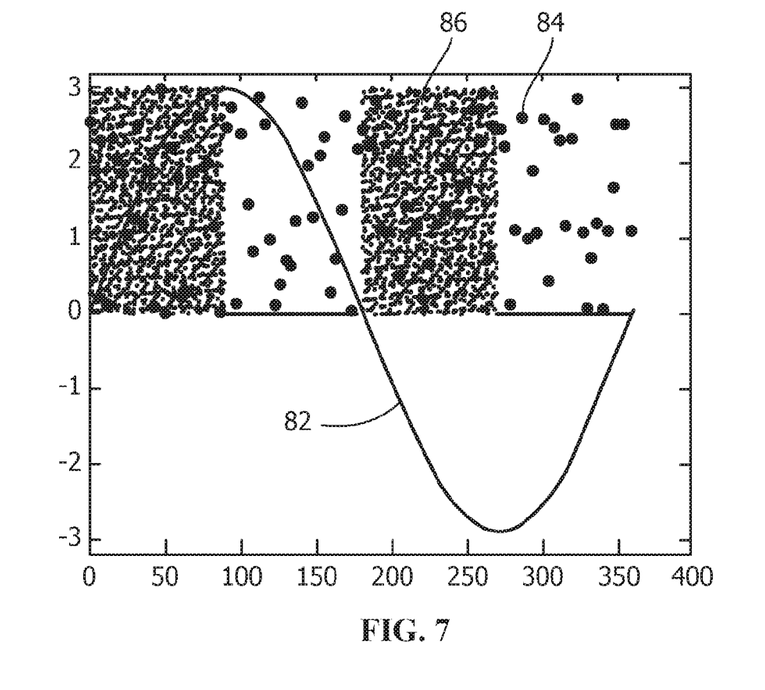
FIG. 7 is a plot of acoustic emission signals measured by acoustic emission sensors and synchronized with the electrical signals of FIG. 6.

In some embodiments, the method monitors a system in situ in real time. In some embodiments, a system monitors electric generator components in real time. On-line partial discharge testing may allow for trending and analysis of electrical equipment. An examination of the partial discharge activity relative to the 360 degrees of an AC cycle allows for identifying a prominent root cause of partial discharges such that appropriate corrective actions may be implemented. The fact that PD events always occur during the first and third quarters of the AC cycle, as shown in FIG. 7, helps AE and PD systems to benefit from each other in better classifying PD events and AE events. On-line partial discharge testing may detect insulation in the progressive phases of deterioration, with trending being able to identify problems long before an eventual failure.

In other embodiments, the method monitors a system for quality control or inspection purposes during a time at which the system may be off-line or shut down or during production of the system. In some embodiments, the system measures exaggerated negative polarity pulses under positive charging and measures exaggerated positive polarity pulses under negative charging. In some embodiments, the system monitors during factory/outage high-potential (hipot) testing and insulation quality control (QC) testing. Hipot testing, as used herein, refers to a class of electrical tests to verify the condition of the electrical insulation in an electrical system. In some embodiments, hipot testing involves applying a high voltage and monitoring the resulting current flowing through the insulation to determine whether the insulation is sufficient to protect from electrical shock. In some embodiments, insulation quality control acoustic emission data is collected. This data may be used to supplement a hipot test. In some embodiments, the methods are applied in-service during an outage. In some embodiments, quality control acoustic emission data supplements a hipot test. In some embodiments, an AE system and/or a PD system is applied in-service during an outage.

In some embodiments, the PD monitoring of an electric generator system is enhanced using AE data to predict and prevent a potential future failure of the system. In some embodiments, an AE system records AE signals as AE data, extracts features, and classifies statistical events using a pattern recognition method. In some embodiments, a PD system collects and records electrical data, extracts features, and classifies statistical events using a pattern recognition method. In the case of a fatigue cracking event, the AE system interprets the AE data to determine the damage condition caused by the fatigue cracking event. In the case of a PD event, the AE system and the PD system work together by fusing the AE data and the PD electrical data to interpret the damage condition caused by the PD event. Any appropriate data fusion method may be used within the spirit of the present invention.

In some embodiments, the AE system and PD system together form an integrated system for detecting fatigue cracking events and partial discharge events. An AE system and a PD system monitoring in combination offers data fusion from a PD event, which helps the PD system and the AE system benefit from each other and leads to enhanced measurement and characterization of the PD event. In some embodiments, a rapid decrease in measured PD intensity serves as an indication of an impending failure of the monitored system.

In some embodiments, an AE system monitors one or more components of an electric generator in real time for PD events and fatigue cracking events. In some embodiments, AE system data enhances a PD measurement system. In some embodiments, PD system data enhances an AE system. In some embodiments, feature extraction and pattern recognition from AE and/or PD system data provides PD and fatigue crack-related event classification. In some embodiments, adaptive machine learning enhances the integrated monitoring system. In some embodiments, quality control acoustic emission data is collected.

Since AE detection is not sensitive to electrical noise, it is more effective at detecting smaller PD events than the PD monitoring system in an electric generator system. Whereas PD monitoring systems tend to only start detecting PD events after significant damage has occurred, an AE monitoring system is capable of detecting PD events and hence monitoring damage at an earlier stage to be able to prevent failure more effectively.

Signal processing and feature extraction may include extraction of peak amplitude 66, frequency, counts or hits 68 above a threshold 60, duration 62, and rise time 64 from the collected data. In some embodiments, data fusion and adaptive machine learning enhance PD measurement and characterization based on AE system data and PD system data.

In some embodiments, the ratio of events detected by the AE detection system and events detected by the PD detection system is determined and monitored as a function of time. If the ratio remains fairly constant, it may be assumed that the detected events are PD events. If, however, the ratio is increasing in time, the expectation is that something that is not a PD event is occurring, which may indicate the occurrence of one or more fatigue cracking events.

In some embodiments, regardless of whether the monitoring system monitors in real time or under inspection conditions, the monitoring system may include decision-making protocols for evaluating whether the monitored system or component is in an acceptable condition or in an unacceptable condition or is safe for continued operation or must be shut down for repairs or maintenance.

The systems and methods may be applied to any electrical systems, including, but not limited to, high power electric generator systems, low power electric generator systems, electrical motors, or transformers.

Example 1

An AE monitoring system and a PD monitoring system were tested in combination on a metal bar serving as a model electric generator system. The monitoring system included transducers, an amplifier, and an oscilloscope. A Tesla coil was used to produce arcing to a predetermined location on the metal bar to simulate a PD event. ASTM E976 ("Standard Guide for Determining the Reproducibility of Acoustic Emission Sensor Response") was followed to break a pencil lead against the predetermined location on the metal bar to simulate a fatigue cracking event. The 2H, 0.5-mm diameter pencil lead extended about 3 mm through a guide ring prior to the lead break. Sensors were located on both sides of the predetermined location on the metal bar and collected AE monitoring system data and PD monitoring system data.

Figure 4:
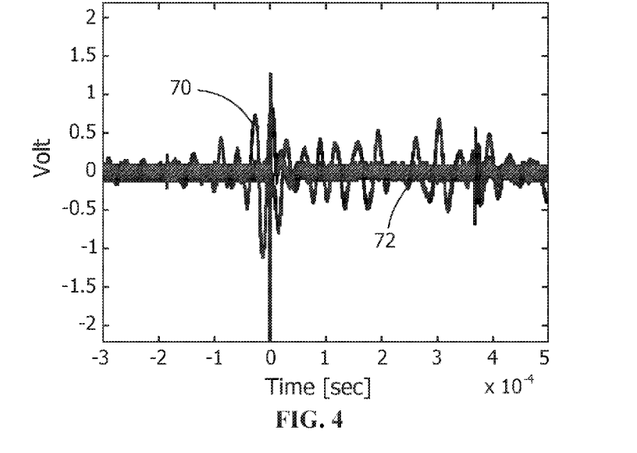
FIG. 4 is a plot of acoustic emission signals for a fatigue cracking event and a partial discharge event in an embodiment of the present disclosure.
Figure 5:
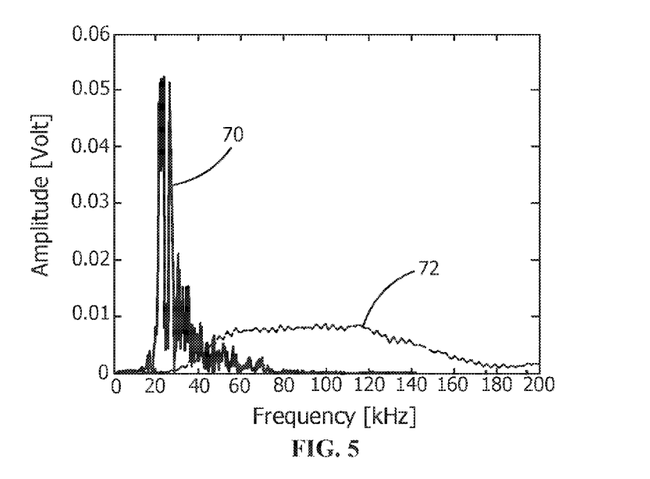
FIG. 5 is a frequency spectrum plot of the acoustic emission signals of FIG. 4.

The AE monitoring system was able to detect signals from both the AE event and the PD event, whereas the PD monitoring system was only able to detect signals from the PD event. Since the PD and fatigue cracking events occurred between the AE sensors, it was possible to calculate the location of the events based on the timing ("time of flight") of the signals reaching the AE sensors. Some of the resulting AE data from these tests is shown in FIG. 4 and FIG. 5. FIG. 4 and FIG. 5 are based on the same AE sensor data, with the voltage as a function of time in FIG. 4 and as a function of frequency in FIG. 5. The AE data 70 from the crack event showed several strong peaks in the low frequency range of about 20 to about 30 kHz. The AE data 72 from the PD event showed a broad weak peak in the higher frequency range of about 60 to about 120 kHz.

Example 2

Figure 6:
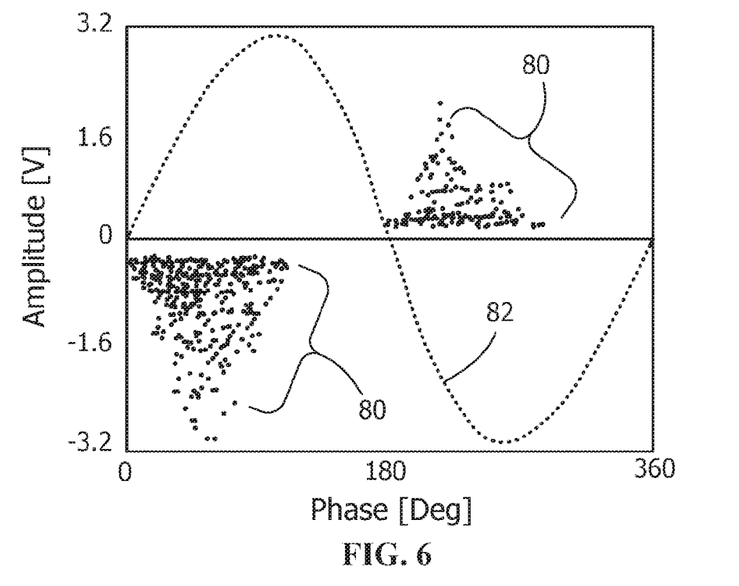
FIG. 6 is a plot of electrical signals measured by partial discharge sensors in an embodiment of the present disclosure.

Sample data from a PD monitoring system and an AE monitoring system, synchronized and monitoring the same sample, show how data fusion allows an AE monitoring system to benefit from a PD monitoring system, and vice versa. A plot of electrical signals 80 measured by the partial discharge sensors is shown in FIG. 6 as a function of AC phase 82. An artificial plot of expected acoustic emissions signals from the same sample as measured by the AE sensors and synchronized with the electrical signals is shown in FIG. 7. The crack event data 84 from the AE sensors is corroborated by the absence of any associated signals from the PD sensors, and the PD event data from the PD sensors is corroborated and enhanced by the associated AE signals 86 from the AE sensors.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of monitoring an electrical system for statistical events, the method comprising:
   synchronizing an acoustic emission monitoring system comprising a plurality of acoustic emission sensors located on a component of the electrical system with a partial discharge monitoring system comprising a plurality of partial discharge sensors located on the component of the electrical system;
   directing collection by the acoustic emission sensors of acoustic emission signals from the component as acoustic emission data and directing collection by the partial discharge sensors of electrical signals as electrical data during an occurrence of a statistical event; and
   fusing and performing pattern recognition of the acoustic emission data and the electrical data to detect and classify the statistical event as a fatigue cracking event or a partial discharge event in the electrical system.

2. The method of claim 1, wherein the statistical event comprises the partial discharge event, the method further comprising determining from the acoustic emission data and the electrical current data a location and a damage condition resulting from the partial discharge event.

3. The method of claim 1, wherein the statistical event comprises the fatigue cracking event, the performing comprising classifying the statistical event as the fatigue cracking event by the pattern recognition of the acoustic emission data.

4. The method of claim 3 further comprising determining from the acoustic emission data a location of the fatigue cracking event and a damage condition of the component resulting from the fatigue cracking event.

5. The method of claim 1 wherein the electrical system comprises an electric generator system.

6. The method of claim 1 wherein the pattern recognition occurs in real time.

7. The method of claim 6 further comprising implementing adaptive machine learning to enhance the pattern recognition.

8. The method of claim 1 wherein the acoustic emission sensors comprise fiber optic acoustic emission sensors.

9. A method of monitoring an electric generator system, for statistical events, the method comprising:
   directing synchronized collection of:
      acoustic emission signals from the component as acoustic emission data by a plurality of acoustic emission sensors located on a component of the electrical generator system; and electrical signals from the component as electrical data by a plurality of partial discharge sensors located on the component of the electric generator system;

evaluating the acoustic emission data to identify acoustic events and the electrical data for electrical events; and monitoring a ratio of acoustic events to electrical events over time and reporting increases in the ratio as fatigue cracking events.

10. The method of claim 9 further comprising determining from the acoustic emission data a location of the fatigue cracking event and a damage condition resulting from the fatigue cracking event.

11. The method of claim 9 wherein the partial discharge sensors comprise fiber optic acoustic emission sensors.

12. The method of claim 9 further comprising:

synchronizing the acoustic emission sensors with the partial discharge sensors; and confirming the fatigue cracking event by pattern recognition of the electrical data.

13. An electrical system monitoring system comprising:

an acoustic emission monitoring system comprising a plurality of acoustic emission sensors locatable on a component of the electrical system;

a partial discharge monitoring system comprising a plurality of partial discharge sensors locatable on a component of the electrical system and synchronized with the acoustic emission monitoring system; and a computer receiving acoustic emission data from the acoustic emission sensors and electrical data from the partial discharge sensors, wherein the computer is configured to:

evaluate the acoustic emission data and the electrical data to identify an occurrence of a statistical event in the component;

fuse and perform pattern recognition of the acoustic emission data and the electrical data to classify the statistical event as a fatigue cracking event and determine a crack location and a crack damage condition resulting from the fatigue cracking event or as a partial discharge event and determine a discharge location and a discharge damage condition resulting from the partial discharge event; and report the statistical event as the fatigue cracking event at the crack location with the crack damage condition or as the partial discharge event at the discharge location with the discharge damage condition.

14. The electrical system monitoring system of claim 13 wherein the acoustic emission sensors collect the acoustic emission data from acoustic emission signals and the partial discharge sensors collect the electrical data from electrical signals from a component of an electric generator system.

15. The electrical system monitoring system of claim 13 wherein the computer receives acoustic emission data from the acoustic emission sensors and electrical data from the partial discharge sensors in real time.

16. The electrical system monitoring system of claim 13 wherein the partial discharge sensors are selected from the group consisting of ultra-high frequency sensors, high frequency current transformers, transient earth voltage sensors, coupling capacitors, and combinations thereof.

17. The electrical system monitoring system of claim 13 wherein the acoustic emission sensors comprise fiber optic acoustic emission sensors.

18. The electrical system monitoring system of claim 13 wherein the computer is configured to conduct the pattern recognition in real time.

* * * * *